(12) United States Patent
Reif et al.

(10) Patent No.: US 9,204,963 B2
(45) Date of Patent: Dec. 8, 2015

(54) STABILIZING IMPLANT WITH EXPANDABLE SEGMENTS

(71) Applicant: Gyrus ACMI, Inc., Southborough, MA (US)

(72) Inventors: Matthias O. Reif, Philadelphia, PA (US); Troy Hemme, Minneapolis, MN (US)

(73) Assignee: Gyrus ACMI, Inc., Southborough, MA (US)

( * ) Notice: Subject to any disclaimer, the term of this patent is extended or adjusted under 35 U.S.C. 154(b) by 317 days.

(21) Appl. No.: 13/815,627

(22) Filed: Mar. 13, 2013

(65) Prior Publication Data

US 2014/0277441 A1    Sep. 18, 2014

(51) Int. Cl.
*A61F 2/20* (2006.01)
*A61B 19/00* (2006.01)
*A61M 39/02* (2006.01)

(52) U.S. Cl.
CPC . *A61F 2/20* (2013.01); *A61B 19/24* (2013.01); *A61F 2250/0003* (2013.01); *A61F 2250/0004* (2013.01); *A61F 2250/0034* (2013.01); *A61F 2250/0048* (2013.01); *A61F 2250/0059* (2013.01); *A61M 39/0208* (2013.01)

(58) Field of Classification Search
CPC .............. A61F 2/20; A61F 2250/0059; A61F 2250/0004; A61F 2250/0034; A61F 2250/0048; A61F 2250/0003; A61B 17/24; A61B 19/24; A61M 39/0208
See application file for complete search history.

(56) References Cited

U.S. PATENT DOCUMENTS

| | | | |
|---|---|---|---|
| 5,016,647 A | 5/1991 | Sanders | |
| 5,197,982 A * | 3/1993 | Goldsmith et al. | 623/9 |
| 5,549,673 A | 8/1996 | Beale | |
| 6,030,350 A | 2/2000 | Jiang et al. | |
| 6,334,441 B1 | 1/2002 | Zowtiak et al. | |
| 6,526,977 B1 | 3/2003 | Gobel | |
| 6,802,317 B2 | 10/2004 | Gobel | |
| 8,052,693 B2 | 11/2011 | Shahian | |
| 8,439,890 B2 | 5/2013 | Beyar et al. | |
| 2006/0058574 A1* | 3/2006 | Priewe et al. | 600/29 |
| 2006/0246033 A1 | 11/2006 | Ninan | |
| 2007/0161322 A1 | 7/2007 | Carmon | |
| 2012/0150293 A1* | 6/2012 | Hoffman et al. | 623/9 |

* cited by examiner

*Primary Examiner* — Christine H Matthews
*Assistant Examiner* — Joshua D Lannu
(74) *Attorney, Agent, or Firm* — Gyrus ACMI, Inc.; Allison Dianis (57) ABSTRACT

An article and method are presented wherein an implant member is provided that is expandable in at least one direction, the implant adapted for use within an area adjacent vocal folds of a patient, the implant member comprising two or more segments, and a subcutaneous access port providing access for injection of a bulking agent into the implant member.

8 Claims, 6 Drawing Sheets

FIG. 1

NORMAL VOCAL CORDS

FIG. 2A

NORMAL VOCAL CORDS

FIG. 2B

VOCAL CORDS WITH PHONATION PROBLEMS

STABILIZING IMPLANT WITH EXPANDABLE SEGMENTS

FIELD OF THE INVENTION

The present invention relates to an article and method for improving phonation ability of a patient, more particularly to an article and method for providing a segmented stabilizing implant adjacent to the vocal folds.

BACKGROUND

It is well known that the ability of a person to speak is a basic need in society. One of the basic structures in the human body that allow for speech is the vocal folds (also known as "vocal cords") located in the larynx and basically are twin infoldings of mucous membranes stretched horizontally across the larynx. Vocal folds, under normal circumstances, vibrate when a person attempts to speak, in a phenomenon known as phonation. The rhythmic opening and closing of the vocal folds provide a major component of human speech. Normally, the folds are pushed apart by subglottal pressure, with the inferior part of each fold leading the superior part. When one or both of the vocal folds fails to function correctly, a person may lose the ability to speak or sing. It is well known that vocal fold dysfunction can range from insufficient movement of the vocal folds to complete vocal fold paralysis. In one vocal fold dysfunction, spasmotic dysphonia, the vocal cords undergo sudden involuntary muscle movements forcing them open or closed and thereby inhibiting the ability to properly phonate. Other factors can affect phonation ability including tumors, muscle tension, or the distance between the vocal cords.

Various devices and methods of treating dysfunctional vocal folds have been developed during the mid to late $20^{th}$ century and continue to be developed today. One known method uses bulking agents (injected directly into the area around the vocal folds) to support paralyzed or dysfunctional vocal folds. These agents may improve and/or restore the ability to speak in patients with vocal fold dysfunction. Bulking agents used in the past include autologous fat, artificial materials such as hyaluronic acid (HA), radiesse gel, calcium hydroxylapatite, biodegradable microspheres, etc. The challenge with traditional bulking agent injection is that injecting the exact amount of required material is a difficult task. It is possible for too little or too much material to be injected as well for the material to end up in a non-ideal location. Injection of bulking agents in an incorrect amount or location for the application of supporting the vocal folds can result in incomplete correction of phonation problems. The outcome of the procedure is highly dependent upon the skill set of the surgeon performing the procedure and the likelihood of a non-ideal dose of bulking material being administered is high.

In-office bulking agent injection is a procedure which is typically performed under local anesthesia and can provide some level of real-time feedback of how well phonation is improved using an endoscope for visualization. Normally, bulking agents have a limited useful lifespan for the patient, which can range anywhere from about six months to about two years, so this treatment has to be repeated periodically. This method does not offer any post-procedure customization opportunity to further improve phonation.

Another known device and method utilize solid shim-like devices fitted proximal to the vocal folds and adapted to provide support to the folds. One commercial example is the VoCom thyroplasty system, manufactured by Olympus. These shims (also known as hydroxylapatite implants) can vary in size and offer medialization for unilateral vocal fold paralysis. Typically vocal fold displacement can range from about 3-8 mm with the implants and about 0-3 mm with the shims. This system and other comparable devices offer a more permanent solution than bulking agents, and can have an indefinite useful lifespan. Implantations of these solid shim-like devices typically take place local anesthesia and do offer some level of real-time feed-back in regards to phonation. One advantage of this implant treatment may be that placement can generally be better controlled compared to bulking injections. This method does not offer any post-procedure customization opportunity to further improve phonation.

The present invention may be generally described as a device and method that may be precisely placed in proximity to the vocal folds (with a patient under local or general anesthesia). It also can provide improved real-time phonation feedback during the procedure as well as the opportunity for post-procedure adjustments.

SUMMARY OF THE INVENTION

The present invention may be used to address one or more of the issues presented above, for example as a vocal fold stabilization device to improve the phonation abilities of a patient. Advantageously, the present invention may be used as a temporary or permanent treatment option. It is contemplated that the present invention (e.g. an implant member) may be adjustable in at least one direction, for example via filling with a bulking agent (or removing such agents), or through a mechanical expansion/contraction of mechanical structure(s) within the implant member. It is contemplated that the implant member include a single adjustable segment, but more preferably include two or more adjustable segments. It is also contemplated that adjustments can be done during and/or after the implantation procedure. Alternatively, it is contemplated that the present invention may be used for stabilization or support of other body tissues where appropriate.

In one exemplary embodiment, an implant member with at least two segments is used to provide support for the vocal cords. The implant member is sized to fit the patient and then surgically placed adjacent the vocal cords of a patient. Each segment is filled with a bulking agent using a medical grade single use syringe through the subcutaneous access port which is in fluid communication with the segments. The filling of the segments of the implant creates a wedge which thereby pushes one vocal cord toward the patient's midline to limit the distance of travel from one vocal cord to the other during active phonation. It is contemplated that vocal cord stabilization may be a key component in improving the phonation process for patients with vocal cord limitations and, therefore, the substance(s) used to fill the segmented implant should provide a certain frequency response and should be of a certain viscosity in order to deliver the best results. It is believed that the liquid(s) selected and the viscosity of the liquid(s) for injection into the implant may create a tailored patient-specific solution to phonation problems.

In another embodiment, stabilization may be possible through a mechanical stabilizing structure, which may be expandable within individual segments of the implant member. The implant is sized and placed surgically and adjustment is possible both during and after the surgical procedure. Various types of mechanical expansion systems are contemplated, including spring-loaded systems with a mechanism for adjustment both during the surgical procedure and after the patient is awake. Alternative stabilization systems may include systems which expand under specific pressures, temperatures or when in contact with certain fluids to provide a support mechanism within the vocal folds.

Accordingly, pursuant to one aspect of the present invention, there is contemplated an article, comprising an implant member that is expandable in at least one direction, the implant adapted for use within an area adjacent vocal folds of a patient; the implant member comprising two or more segments; and a subcutaneous access port providing access for injection of an agent into the implant member.

The invention may be further characterized by one or any combination of the features described herein, such as the two or more segments are independently fillable; the two or more segments are filled or adjusted to an optimum shape and volume to achieve an ideal level of phonation for a given patient; the bulking agent is saline; the bulking agent is liquid silicone; the implant member is filled with liquids of different viscosities; the implant member is made of plastic; the implant member is a permanent implant; or the implant member is a temporary implant.

Accordingly, pursuant to one aspect of the present invention, there is contemplated an article, comprising an implant member that is expandable in at least one direction, the implant adapted for use within an area adjacent vocal folds of a patient; the implant member comprising two or more segments; and a subcutaneous access port for providing access for adjusting a mechanical stabilization mechanism within the implant member.

The invention may be further characterized by one or any combination of the features described herein, such as the mechanical stabilization mechanism consists of a spring-based support system; the mechanical stabilization mechanism consists of a support system which is expandable by adjusting pressure, temperature, or addition of a fluid; the implant member is made of plastic; the implant member is a permanent implant; or the implant member is a temporary implant.

Pursuant to another aspect of the present invention, there is contemplated a method of implanting a vocal cord bulking system, comprising inserting an implant member with two or more segments adjacent vocal folds of a patient; inserting a subcutaneous access port to access contents of the implant member through a neck of the patient; and filling, draining, or adjusting the implant member through the subcutaneous access port to encourage improved phonation.

DESCRIPTION OF THE DRAWINGS

The drawings described herein are for illustration purposes only and are not intended to limit the scope of the present disclosure in any way.

DETAILED DESCRIPTION OF THE INVENTION

Implant Member

Functionally, the implant member is expandable in at least one direction and is adapted for use in an area adjacent the vocal cords of a patient. The implant member, being located in an area adjacent to the vocal folds, or other tissue of interest, need not be in direct contact with the vocal cords or other tissue, but rather next to the vocal cords or tissue without necessarily making physical contact.

The implant member may be any biocompatible, implantable material. The implant member may be composed of any nontoxic, flexible plastic material impermeable to liquid or gas, such as a medical grade silicone elastomer or an organo siloxane copolymer, or any equivalent material. In the case of use with a bulking agent, the flexible plastic may be more elastic. In the case of use with a mechanical expansion system, the plastic may be more durable and rugged. In either case, the material used may have an elastic limit beyond which the implant cannot expand. This feature in combination with sizing the implant appropriately will ensure that the tissue region that is to be adjusted, moved, supported or otherwise repositioned will not be moved beyond desired or reasonable limitations.

The implant member may be sized appropriately to fit in a desired space in order to apply pressure along the surface area of the tissue of interest. In the case of vocal cords, contact is typically desired along the entire region of vocal cord limitation, which may include the entire length and width of the vocal cord.

The desired size of the implant member may be measured intraoperatively using sizing templates. Alternatively, the implant may be sized preoperatively using various imaging modalities including but not limited to X-ray, CT, MRI, and ultrasound.

A horizontal slice of the implant is typically wider at one end and narrower at another. A vertical slice of the implant is typically roughly consistent along its length, with variations as necessary depending on the exact vocal cord limitation to be overcome. Alternatives and variations to specific implant shaping would be obvious to one of ordinary skill in the art.

Segments

Functionally, the two or more segments of the implant member provide increased flexibility to effectively correct phonation problems. Depending on the nature of the vocal cord limitation, the vocal cord of interest may be adjusted, moved, supported or otherwise repositioned differentially along its length and width using different pressures or fluid viscosities.

The segments may be linked at a minimum of one connection point, but various connection points are possible. The connection may be formed by the same material or a different material as the implant member itself. Channels or other connections means may be provided between the balloon segments to allow intermixing there between, if it is so desired.

Subcutaneous Access Port

Functionally, the one or more subcutaneous access ports provide access for injection of a bulking agent into or adjustment of a mechanical stabilization scheme within the implant member.

One or more access ports may be subcutaneously placed in the neck of a patient providing access to the implant member located adjacent the vocal cords of a patient. In the case where the segments are independently fillable or adjustable, multiple access ports may be provided. A valving scheme may be set up via the subcutaneous access port to independently access each segment within the implant member.

For the case of use of the implant member with bulking agents, bulking agent(s) of choice may be drawn into a syringe, the syringe placed into a port within the subcutaneous access port system, and changes in the phonation of the patient are evaluated to determine whether more or less bulking agent is needed or if additives need to be supplemented into a given port to adjust for viscosity, pressure, or frequency response. Different bulking agents can be injected with a syringe into individual access ports or via the valving scheme with access corresponding to a given segment.

The subcutaneous access port allows for filling and emptying of each segment within the implant following the surgical implantation of the implant member. With the patient awake during the filling process, active feedback is provided as to the level of correction of the vocal cord limitation. Both the quantity of bulking agent(s) as well as the viscosity of the bulking agent(s) can be adjusted to meet a specific frequency response or achieve a certain amount of wedging pressure between tissues. Additives supplied within the segments of the implant allow for adjusting viscosity as needed. Possible additives might include substances such as polymers (i.e. ethyl-butyl-polymer, Butyl cyanoacrylate, or the like), jelly or powder compounds, glazes, or any other substance capable or appropriately adjusting viscosity to produce a desired effect inside the body.

For the case of mechanical stabilization of the implant member, cranks, handles, or cams may be provided for making adjustments to the stabilization scheme (i.e. expanding the spring-based system). These adjustment means may be hidden away after adjustment within the subcutaneous access port.

Bulking Agents and Viscosities

Functionally, bulking agents are used in the present invention to expand the volume of the segments of the expandable member and improve phonation ability of a patient. For example, saline, silicone, oil, or gas may be used as bulking agents. Multiple bulking agents can be mixed within a given segment of the implant member to create a desired frequency response, viscosity, and pressure. Alternatively, various other fluids, including water or the like, or any manner of additive may be mixed with other bulking agents to create a desired effect.

In certain cases, it may be desirable to perform intraoperative imaging to precisely determine position of the implant and potentially make corrections before closing up the patient. In such a case, it may be desirable to first inject a minimally viscous or non-viscous bulking agent prior to imaging with an imaging modality, which may include ultrasound, X-ray fluoroscopy, intraoperative CT, or intraoperative MRI. Subsequently, once imaging was complete and the implant member was repositioned, if desired, an additive could be supplemented into the implant segments to increase viscosity to a level that may encourage optimal phonation ability.

Higher viscosities yield slower flowing liquids. Viscosity varies inversely with temperature. Higher pressure causes viscosity to increase.

Normal saline is an aqueous solution of NaCl with a concentration of 0.9 percent (weight/volume). Typically, there is little discernable difference between the viscosity of saline and the viscosity of water. The dynamic viscosity of water is $8.90 \times 10^{-4}$ Pa·s or $8.90 \times 10^{-3}$ dyn·s/cm$^2$ or 0.890 cP at about 25° C. Water has a viscosity of 0.0091 poise at 25° C., or 1 centipoise at 20° C.

Silicone's molecular weight is a function of its degree of polymerization (DP)–the number of repeating Si—O—Si units in the polymer. Various inter-related factors affect the viscosity, including: the degree of polymerization, the molecular weight, the length of the polymer. Silicone fluids range in viscosity from 0.65 cs (thinner than water) to more than 20,000,000 cs (thicker than chewing gum).

Oil viscosity can vary largely with temperature and other factors and provides a large range of possibilities for achieving the desired phonation correction.

Mechanical Stabilization

Functionally, the purpose of mechanical expansion and stabilization system of the present invention is to provide a permanent, customizable support system for the vocal cords to allow for better connection there between during phonation, or support for other tissues as necessary.

One embodiment includes the use of a spring-loaded system with a mechanism for adjustment both during the surgical procedure and after the patient is awake. Spring loaded systems may include a platform element and adjustable tension springs. Transverse support members may be provided for additional support. Cables or other linking means may be provided between springs for extra mechanical support. Each segment within the implant can have a different spring tension to provide varying degrees of support as required. A crank, handle, or cam mechanism may be used for tightening or loosening the tension on each spring. A link may be provided across implant segments such that tension adjustments in one chamber might affect tension adjustments in another. The orientation of the spring within each segment of the implant member would affect the potential direction for expansion. It is contemplated that uni-directional expansion will be the m Alternative stabilization systems may include systems which expand under specific pressures, temperatures or when in contact with certain fluids to provide a support mechanism within the vocal folds.

Figure 1:
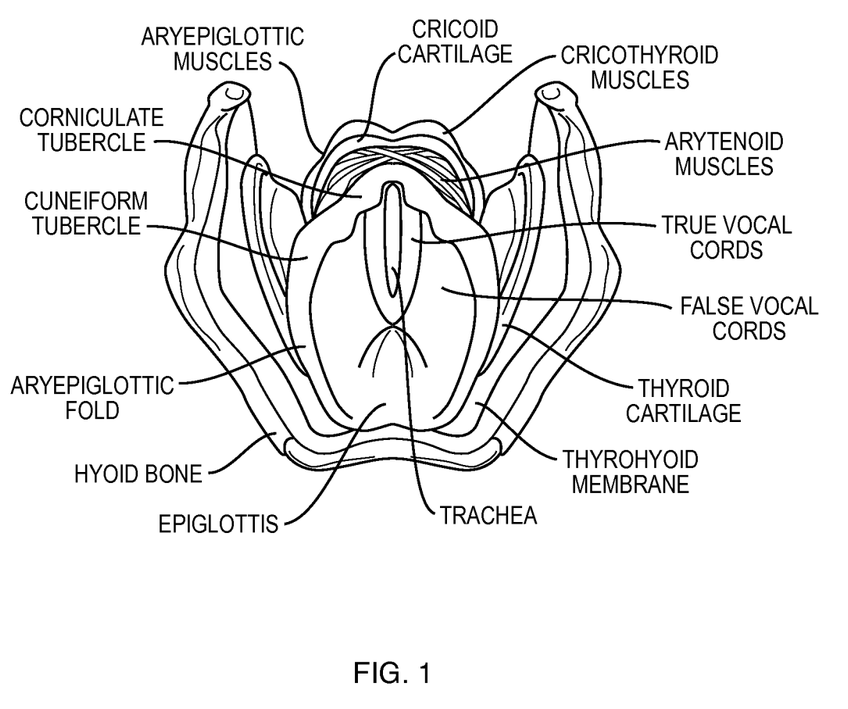
FIG. 1 is a cross-sectional view of a patient's anatomy, detailing different structures within the throat.

Turning now to the drawings to illustrate examples of embodiments of the present teachings, FIG. 1 details the anatomy of interest in the vicinity of the vocal cords, including various muscles, bones, and cartilage.

Figure 2A:
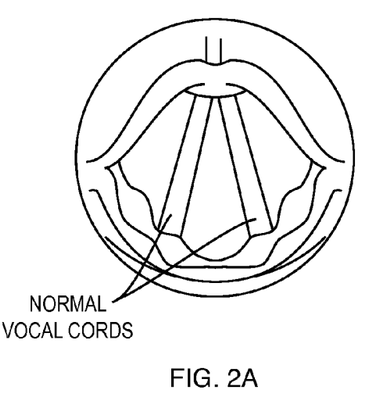
FIGS. 2a-2d are cross-sectional views of the vocal cords in a healthy state, a diseased state, and after medical correction.
Figure 2B:
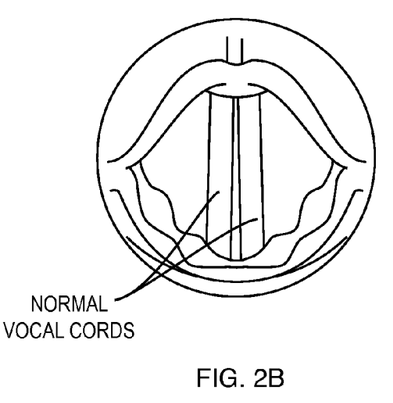
Figure 2C:
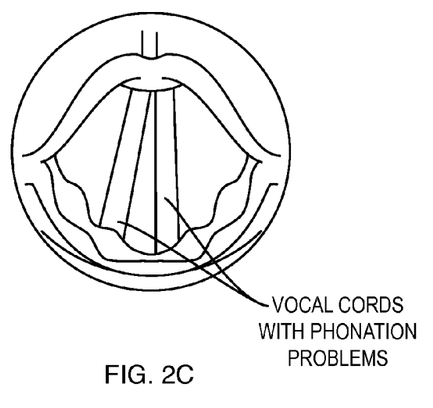
Figure 2D:
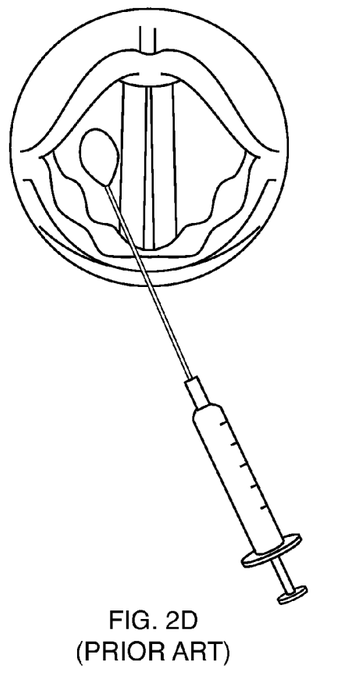

FIGS. 2a-2d illustrate normal vocal cord anatomy with the vocal cords open (FIG. 2a) and closed (FIG. 2b), vocal cord anatomy that needs correction (FIG. 2c), and injection of a bulking agent via a syringe, as in the prior art, to push the misaligned vocal cord back into place (FIG. 2d).

Figure 3:
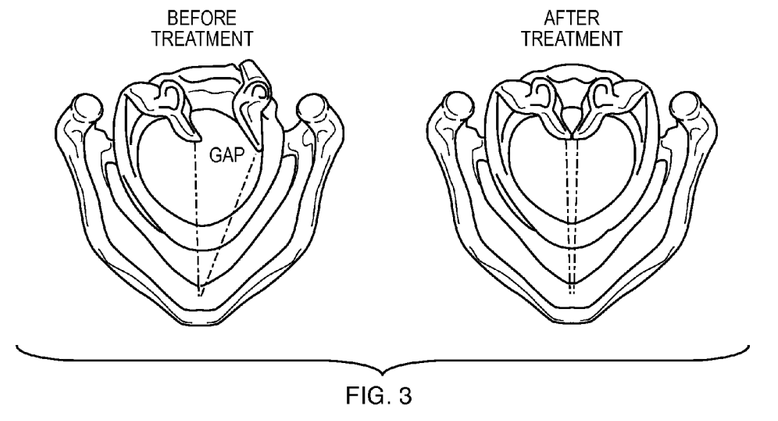
FIG. 3 is a cross-sectional view of a patient's vocal cord anatomy before and after medical intervention.

FIG. 3 shows the cricoid cartilage and arytenoids muscle opening and closing the vocal folds. This action produces tension in the vocal cords. Vocal cord vibration, i.e. opening and closing, is produced from the airflow there through.

Figures 4, 5:
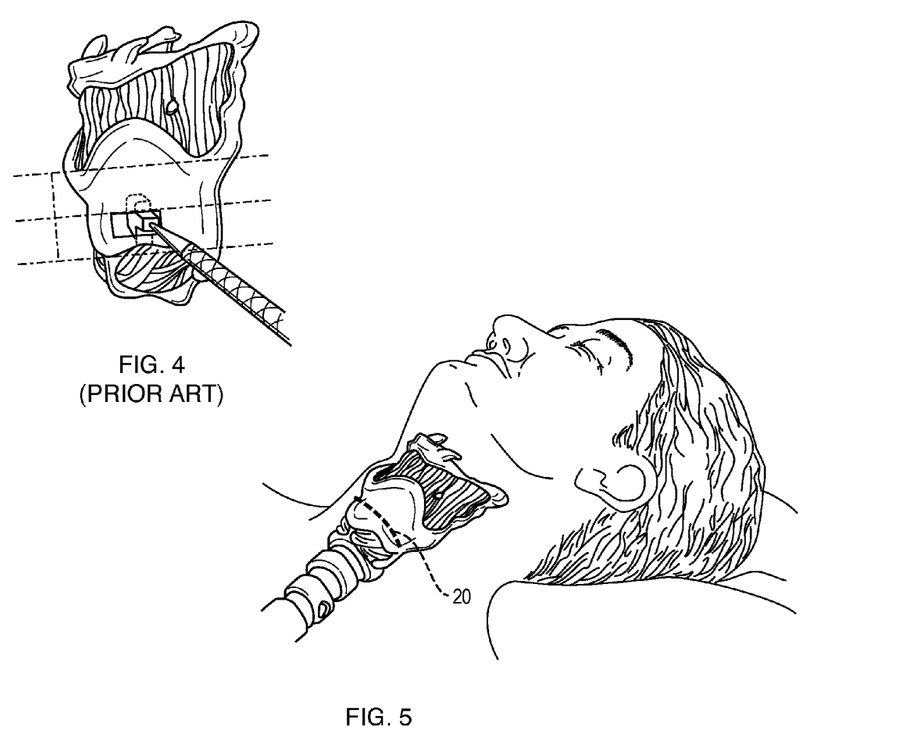
FIG. 4 is a perspective view of a patient's anatomy during placement of a vocal cord implant.
FIG. 5 is a perspective view of a patient's anatomy indicating an optimum location for surgical intervention in accordance with the present invention.

FIG. 4 illustrates placement of a VoCom shim into the vocal folds of a patient (prior art). Surgical placement of the implant member with expandable segments of the present invention would be similar in that an incision would be made in the throat of the patient, while fully anesthetized and lying in a supine position, as in FIG. 5.

Figure 6A:
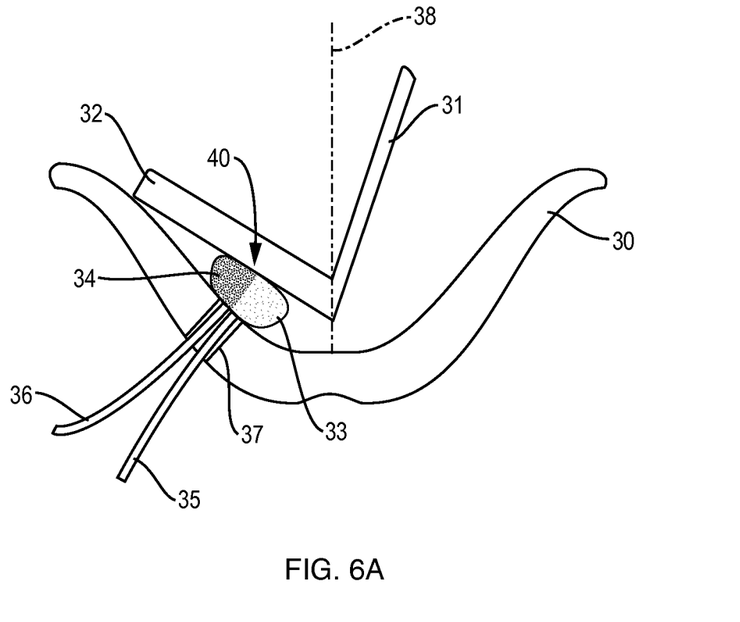
FIGS. 6a and 6b illustrate the vocal cord bulking system in accordance with the present invention.
Figure 6B:
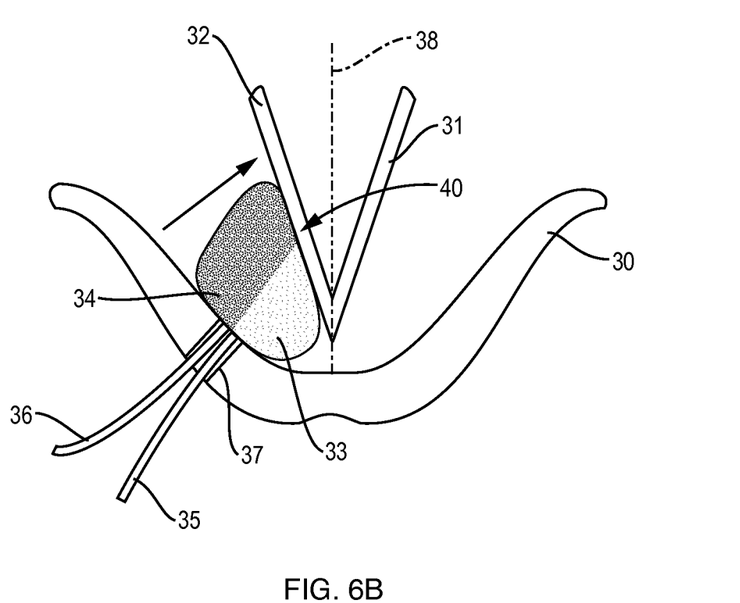
Figure 7A:
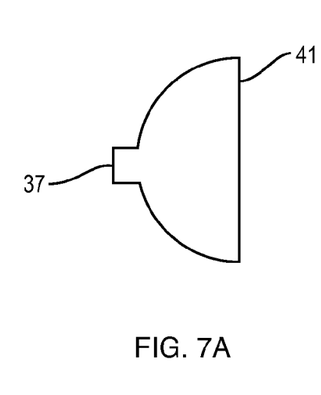
FIGS. 7a-7d are cross-sectional views of a series of alternative embodiments of shape for the vocal cord bulking system of the present invention.
Figure 7B:
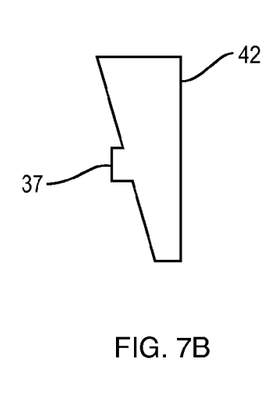
Figure 7C:
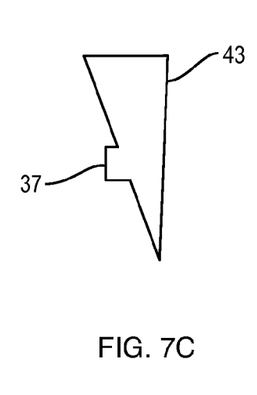
Figure 7D:
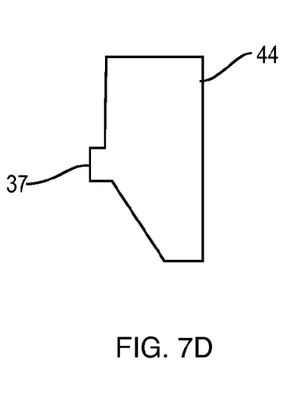
Figure 8A:
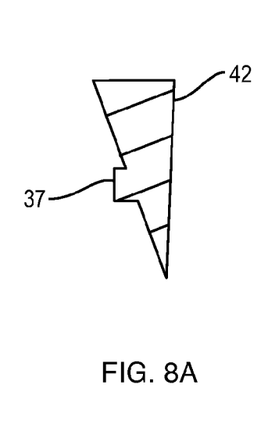
FIGS. 8a-8d are cross-sectional views of the implant member of the present invention illustrating the implant member before and after expansion in different directions.
Figure 8B:
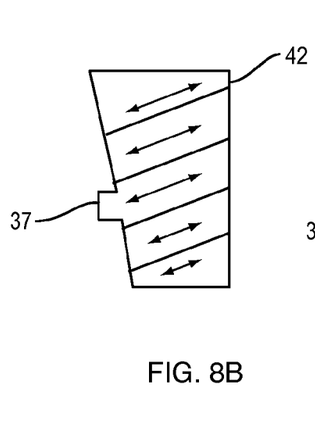
Figure 8C:
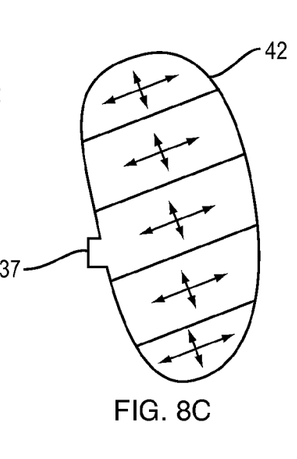
Figure 8D:
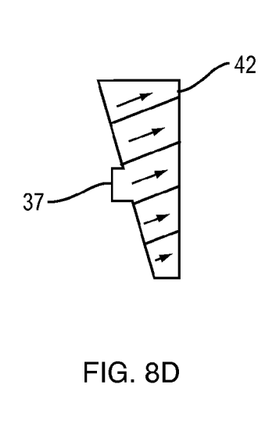

Implant member 40 is inserted in a deflated state adjacent the vocal folds of a patient needing correction. In FIG. 6a, implant segments 33 and 34 are filled with a small amount of bulking agent via subcutaneous access port 37, such that implant member 40 fills the space between vocal cord 32 and cartilage 30. Access to segment 33 is provided through tube 35. Access to segment 34 is provided through tube 36. In FIG. 6b, implant member 40 is expanded to push vocal cord 32 toward midline 38 of the patient to correct the vocal cord defect. The patient may be awake during this portion of the procedure and therefore active feedback is possible. It is contemplated that the present invention, therefore, provides for more precise filling and expansion of the implant member along the surface of vocal fold 32.

It is contemplated that various shapes and sizes of the implant member with expandable segments will be available for surgical implantation. Example cross-sectional slices are shown in FIGS. 7a-7d in accordance with the present invention. The implant may be sized and shaped according to specific patient anatomy and vary depending upon the type of vocal fold limitation to create a customized patient-specific solution.

FIGS. 8a-8d illustrate several chambers for expansion within a given implant member. Potential directions for expansion are indicated. These directions may vary depending on the nature of the vocal fold defect and the type of correction desired.

Figure 9A:
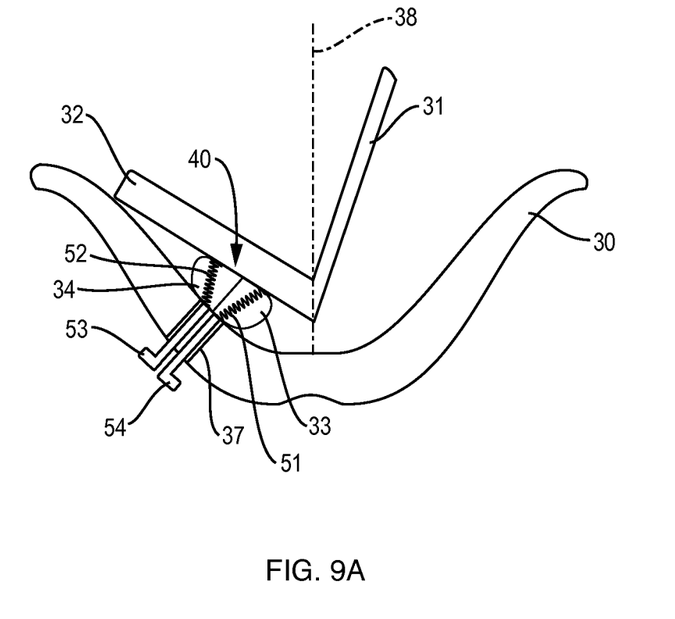
FIGS. 9a-9b are cross sectional views of the implant member of the present invention showing one embodiment of mechanical stabilization.
Figure 9B:
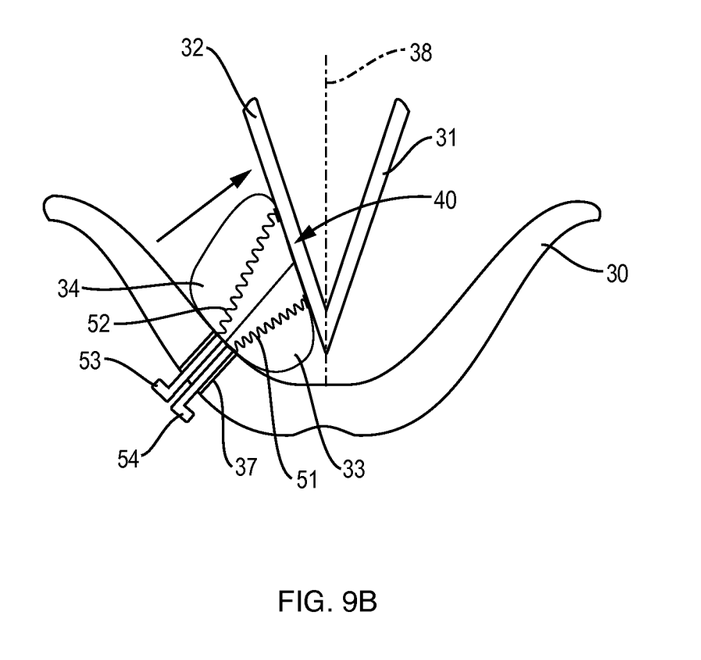

Implant member 40 fitted with one example of mechanical stabilization means is inserted in an unexpanded state adjacent the vocal folds of a patient needing correction in FIG. 9a. In FIG. 9b, springs 51 and 52 are expanded within segments 33 and 34, respectively, using cranks 53 and 54 to such a position that vocal fold 32 is moved to a more optimal position for phonation, i.e. toward midline 38. After adjustment, it is contemplated that cranks 53 and 54 may be compacted into a discreet position within subcutaneous access port 37.

The invention claimed is:

1. An article, comprising:
   an implant member that is expandable in at least one direction;
   the implant member comprising two or more segments, the two or more segments being adjacent to one another; and
   two or more subcutaneous access ports for providing access for adjusting a mechanical stabilization mechanism within the implant member,
   wherein a horizontal slice of the implant is wider at one end and narrower at the other end and a vertical slice is consistent along its length,
   wherein the two or more segments are independently adjustable, and
   wherein the implant member is adapted to support the vocal folds of a patient.

2. The article of claim 1, wherein the mechanical stabilization mechanism consists of a spring-based support system.

3. The article of claim 1, wherein the mechanical stabilization mechanism consists of a support system which is expandable by adjusting pressure, temperature, or addition of a fluid.

4. The article of claim 1, wherein the implant member is made of a material that has an elastic limit beyond which the implant cannot expand.

5. The article of claim 1, further comprising one or more channels between the two or more segments.

6. An article, comprising:
   an implant member that is expandable in at least one direction, the implant adapted for use within an area adjacent vocal folds of a patient;
   the implant member comprising two or more adjacent segments, the two or more segments being linked to each other at a minimum of one connection point; and
   two or more subcutaneous access ports providing access for injection of a bulking agent into the implant member,
   wherein each of the two or more adjacent segments are independently fillable,
   wherein the two or more segments are independently fillable,
   wherein the two or more subcutaneous access ports comprise a tubing pathway and a control mechanism connected to each of the two or more segments.

7. A method of implanting a vocal cord bulking system, comprising:
   inserting an implant member with two or more adjacent segments adjacent vocal folds of a patient, wherein the two or more adjacent segments are independently adjustable;
   inserting two or more subcutaneous access ports to access contents of the implant member through a neck of the patient; and
   filling, draining, or otherwise adjusting the implant member through the subcutaneous access port to encourage improved phonation.

8. The method of claim 7, further comprising adjusting the viscosity of bulking agents to meet a specific frequency response.

* * * * *